United States Patent [19]

Molloy

[11] 4,132,737

[45] Jan. 2, 1979

[54] TRIFLUOROMETHYL SUBSTITUTED 1-AMINOINDANES

[75] Inventor: Bryan B. Molloy, Indianapolis, Ind.

[73] Assignee: Eli Lilly and Company, Indianapolis, Ind.

[21] Appl. No.: 881,301

[22] Filed: Feb. 27, 1978

[51] Int. Cl.$^2$ .............................................. C07C 87/64
[52] U.S. Cl. .................................... 260/578; 260/580; 260/582; 260/590 EA; 260/646; 260/650 F; 260/651 R; 260/651 F; 424/316; 424/330; 560/81; 562/405
[58] Field of Search ................. 260/578; 424/316, 330

[56] References Cited

U.S. PATENT DOCUMENTS

| | | | |
|---|---|---|---|
| 3,637,740 | 1/1972 | Sarges | 260/578 X |
| 3,704,323 | 11/1972 | Krapcho | 260/576 |

OTHER PUBLICATIONS

Aspro–Nicholas Ltd., "Chem. AB.", vol. 62, Ab. No. 16161 d (1965).
Protiva et al., "Chem. AB.", vol. 60, AB. No. 1716 g (1964).

*Primary Examiner*—Winston A. Douglas
*Assistant Examiner*—John Doll
*Attorney, Agent, or Firm*—James L. Rowe; Arthur R. Whale

[57] ABSTRACT

4(5 or 6 or 7)-Trifluoromethyl-1-aminoindanes, useful as inhibitors of N-methyl transferase.

5 Claims, No Drawings

TRIFLUOROMETHYL SUBSTITUTED 1-AMINOINDANES

BACKGROUND OF THE INVENTION

There are many references to 1-aminoindane in the non-patent literature. 1-Aminoindane appears in Beilstein, *Hanbuch der Organ. Chem*, Bd XII, Syst. No. 1709 pg. 1191. Of particular interest is the reference appearing in *Chem. Abstr.* 62, 16161d (1965) which refers to 1-aminoindane derivatives valuable as anti-depressant and psychostimulating agents. The compounds in question are, in general, N-substituted 1-aminoindanes. Horn and Schenider, publishing in *J. Pharm. Exp. Ther,* 180, 523-30 (1972), state that 2-aminoindane is a better inhibitor of catechol amine uptake than 1-aminoindane.

Substituted 1-aminoindanes in which there is a substituent is in the phenyl ring of the indane are known, but the suggested substituents are halogens, methoxy, amino, hydroxy or acetyl (see *Chem. Abstr.,* 60, 1716g (1964) and U.S. Pat. No. 3,637,740 for example). Trifluoromethyl is not one of the suggested substituents.

SUMMARY OF THE INVENTION

This invention provides trifluoromethyl substituted-1-aminoindanes of the formula:

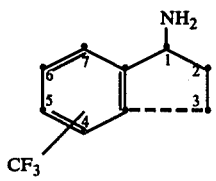

and pharmaceutically-acceptable acid addition salts thereof.

The compounds of this invention are enzyme inhibitors, specifically inhibitors of norephineprine N-methyl transferase, previously referred to as PNMT (phenylethanolamine N-methyl transferase).

The pharmaceutically-acceptable acid addition salts of this invention include salts derived from inorganic acids such as: hydrochloric acid, nitric acid, phosphoric acid, sulfuric acid, hydrobromic acid, hydriodic acid, nitrous acid, phosphorous acid and the like, as well as salts derived from nontoxic organic acids such as aliphatic mono and dicarboxylic acids, phenyl-substituted alkanoic acids, hydroxy alkanoic and alkandioic acids, aromatic acids, aliphatic and aromatic sulfonic acids, etc. Such pharmaceutically-acceptable salts thus include sulfate, pyro-sulfate, bisulfate, sulfite, bisulfite, nitrate, phosphate, monohydrogenphosphate, dihydrogenphosphate, metaphosphate, pyrophosphate, chloride, bromide, iodide, acetate, propionate, decanoate, caprylate, acrylate, formate, isobutyrate, caprate, heptanoate, propiolate, oxalate, malonate, succinate, suberate, sebacate, fumarate, maleate, mandelate, butyne-1,4-dioate, hexyne-1,6-dioate, benzoate, chlorobenzoate, methylbenzoate, dinitrobenzoate, hydroxybenzoate, methoxybenzoate, phthalate, terephthalate, benzenesulfonate, toluenesulfonate, chlorobenzenesulfonate, xylenesulfonate, phenylacetate, phenylpropionate, phenylbutyrate, citrate, lactate, β-hydroxybutyrate, glycollate, malate, tartrate, methanesulfonate, propanesulfonate, naphthalene-1-sulfonate, naphthalene-2-sulfonate and the like salts.

1-Aminoindane represented by the formula

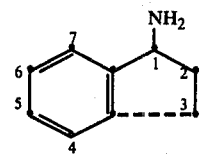

contains an asymmetric carbon atom, carbon atom 1. 1-Aminoindane is ordinarily prepared as a racemate, but this racemate has been resolved into its dl components. This invention provides a 4 or 5 or 6 or 7-trifluoromethyl-1-aminoindane, either as a racemic mixtures or as a pure optical antipode, having the ability to inhibit norephineprine N-methyl transferase.

The compounds of Formula I are prepared by reductive amination of trifluoromethyl substituted 1-indanones (of which the compound of Formula XI in the following Flow Sheet is an example). Reductive amination is a familiar process in organic chemistry, and many reductive amination agents have been described; see, for example, Harrison and Harrison, Compendium of Organic Synthetic Methods, Wiley-Interscience (N.Y., London, Sydney, Toronto, 1971) pp. 258-61.

Some reductive amination agents function by reducing the ketone and inserting the amino group in one step, others by reducing and aminating in separate steps. For example, the following typical reductive amination agents, taken from Harrison and Harrison, (loc. cit.) may be mentioned.

1. Formamide and formic acid;
2. benzylamine in benzene, followed by sodium hydride in tetrahydrofuran, followed by acid;
3. ammonia and lithium cyanoborohydride in methanol;
4. benzylamine, followed by sodium borohydride, followed by hydrogenation;
5. hydroxylamine, followed by sodium dihydrogen metaphosphite and nickel in aqueous ethanol, by nickel-aluminum and sodium hydroxide, by zinc and ammonia, by sodium and ammonia, by lithium aluminum hydride, by diborane, by catalytic hydrogenation, or by electrolytic hydrogenation;
6. hydroxylamine hydrochloride in polyphosphoric acid.

The preferred reductive amination agents for preparing the compounds of Formula I are a mixture of ammonium acetate and sodium cyanoborohydride (see *J. Am. Chem. Soc.* 93, 287-97 (1971); or hydroxylamine hydrochloride and pyridine, followed by acetic anhydride, followed by reduction, preferably with diborane as illustrated in the Flow Sheet. All of the steps of the preferred reactions are carried out in inert solvents such as alkanols and ethers, of which ethanol, methanol and tetrahydrofuran are preferred.

The various reaction steps are carried out at moderate temperatures, such as from 0° C. to 60° C. In general, temperatures from 0° C. to the ambient temperature are preferred.

The compounds of this invention are prepared by a single synthetic procedure, the final product depending solely upon the nature of the starting material. The following Flow Sheet illustrates the preparation of one of the four aminoindane bases of this invention, 6-trifluoromethyl-1-aminoindane.

FLOW SHEET

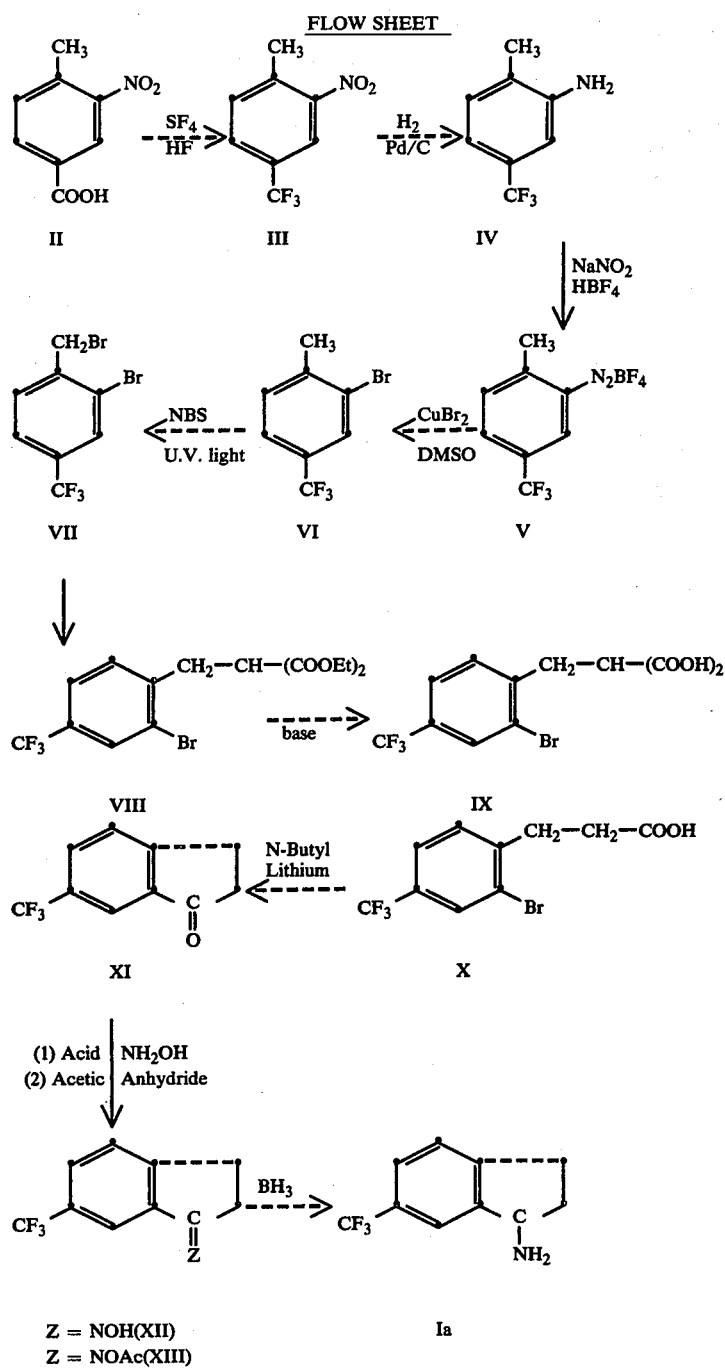

Z = NOH(XII)
Z = NOAc(XIII)

According to the procedure illustrated in the Flow Sheet, a nitromethylbenzoic acid specifically 3-nitro-4-methylbenzoic acid (II) is fluorinated with SF₄ to yield a nitro-trifluoromethyltoluene, specifically 2-nitro-4-trifluoromethyltoluene (III). Reduction of the nitro group to an amine group by catalytic hydrogenation yields an aminotrifluoromethyltoluene, specifically 4-trifluoromethyl-2-aminotoluene (IV). Diazotization of this compound and reaction of the diazonium fluoroborate salt with cuprous bromide or other source of bromide ion yields a trifluoromethylbromotoluene, specifically 4-trifluoromethyl-2-bromotoluene (VI). The methyl side chain is next brominated using N-bromosuccinimide or other suitable source of bromine in the presence of ultraviolet light or a free radical initiator to yield the corresponding benzylbromide, specifically 4-trifluoromethyl-2-bromobenzylbromide (VII). The side-chain bromine is next replaced with an acetic radical (—CH₂—COOH) by reacting the benzyl bromide with malonic ester sodium salt, saponifying the malonic ester and decarboxylating the diacid thus formed. The product of this series of reactions is β-(4-trifluoromethyl-2-bromophenyl)propionic acid (X). This acid is then cyclized by the procedure of *J. Org. Chem.*, 40, 2398 (1975), to yield a trifluoromethylindanone, specifically 6-trifluoromethylindanone (XI). The indanone can then be converted to the corresponding 1-aminoindane by several different procedures. One illustrated in the Flow Sheet involves the preparation of the corresponding oxime. Acetylation of the oxime, and reduction of the acylated oxime with diborane yields an amino group, specifically 6-trifluoromethyl-1-aminoindane (Ia). An alternative procedure involves the reductive amination of the indanone (XI) with sodium cyanoborohydride in the presence of ammonium acetate or other source of ammonia.

Using the series of reactions in the above flow sheet, if 3-nitro-2-methylbenzoic acid is employed as the starting material, the final product is 4-trifluoromethyl-1-aminoindane. If 2-nitro-3-methylbenzoic acid is employed, the final product is 7-trifluoromethyl-1-aminoindane. If 4-nitro-3-methylbenzoic acid is employed, the final product is 5-trifluoromethyl-1-aminoindane.

The preparation of compounds of this invention are fully illustrated by the following specific examples.

EXAMPLE 1

Preparation of 1-Amino-6-trifluoromethylindane

A reaction mixture was prepared from 90.5 g. of 3-nitro-4-methylbenzoic acid, 162 g. of sulfur tetrafluoride and 30 g. of HF as a catalyst. The reaction mixture was heated at 150° C. overnight in a sealed reaction bottle. The reaction bottle was opened and the contents allowed to remain overnight at ambient temperature during which time a majority of the volatile constituents evaporated. The remaining reaction mixture was dissolved in methylene dichloride and the methylene dichloride solution poured into an ice-water mixture. The organic layer was separated and the aqueous layer extracted twice more with methylene dichloride. The methylene dichloride extracts were combined and the combined extracts washed twice with water, twice with 10 percent sodium carbonate solution, again with water and finally with saturated aqueous sodium chloride solution. The methylene dichloride was dried and the methylene dichloride evaporated therefrom to yield a residue comprising 104.4 g. of 2-nitro-4-trifluoromethyltoluene formed in the above reaction. The residue was distilled through a Vigreaux column. After discarding an initial fraction (weighing 2.5 g.) collected up to 76° C. at 8 torr., two fractions weighing 82.9 g. boiling in the range 76°–8° C. at 8 torr., and a third fraction weighing 5.9 g. and boiling at 78° C. were collected. Each of these latter three fractions consisted of purified 2-nitro-4-trifluoromethyltoluene.

Analysis Calc.: C, 46.84; H, 2.95; N, 6.83; F, 27.78; Found: C, 46.67; H, 2.85; N, 6.93; F, 27.86.

Ten grams of 2-nitro-4-trifluoromethyltoluene were dissolved in 85 ml. of ethanol and the mixture hydrogenated at 60 psi using 5 g. of a 5 percent palladium-on-carbon catalyst. After the uptake of hydrogen equaled the theoretical, the hydrogenation was terminated, and the catalyst removed by filtration. Evaporation of the solvent from the filtrate yielded as a residue an oil which crystallized on standing; m.p. = 31°–3° C., constituting 5-trifluoromethyl-2-methylaniline formed in the above reaction. The residue was distilled through a vigreaux column. The compound distilled within the range 70°–74° C. at 8 torr. Purified 5-trifluoromethyl-2-methylaniline melted at 33°–4° C.

Seventeen and one-half grams of 5-trifluoromethyl-2-methylaniline was melted and the melted material added to 100 ml. of a cold 48 percent HBF$_4$ solution. 7.9 g. of sodium nitrite in 10 ml. of water were added thereto in dropwise fashion. The temperature of the diazotization reaction was maintained below 15° C. during the addition. The diazotization mixture was stirred in the cold for about 15 minutes and then poured onto a sintered glass funnel. 5-Trifluoromethyl-2-methylphenyldiazonium fluorborate formed in the above reaction was collected thereon as a solid precipitate. The filter cake was washed once with cold HBF$_4$ solution, twice with cold ethanol and several times with cold ether; weight = 20.2 g.; m.p. above 250° C.

A solution was prepared from 23.4 g. of cupric bromide and 225 ml. of DMSO in a 1000 ml. round bottom flask. The mixture was stirred vigorously. Next, 14.4 g. of 2-methyl-5-trifluoromethylphenyldiazoniumfluoborate in 100 ml. of DMSO were added to the cupric bromide solution over a period of about 30 minutes while maintaining the temperature in the range 25°–30° C. After the addition had been completed, the reaction mixture was poured over 1 liter of an ice-water mixture. The aqueous solution was extracted three times with ether. The ether extracts were combined and the combined extracts washed with water and with saturated aqueous sodium chloride. The ether solution was dried and the ether removed by evaporation to yield 9.0 g. of a yellow oil containing 2-bromo-4-trifluoromethyltoluene formed in the above reaction. Distillation of the residue through a Vigreaux column yielded 4.2 g. of purified 2-bromo-4-trifluoromethyltoluene boiling in the range 58°–49° C. at 10 torr.

Analysis Calc.: C, 40.20; H, 2.53; Br, 33.43; Found: C, 40.44; H, 2.57; Br, 33.18.

A solution of 23.9 g. of 2-bromo-4-trifluoromethyltoluene and 19.6 g. of N-bromosuccinimide was prepared in 285 ml. of carbon tetrachloride. The reaction mixture was irradiated with ultraviolet light for about 4 hours while being heated to reflux. The reaction mixture was then cooled to below 10° C. and the succinimide by-product removed by filtration. The organic layer was washed with water and then dried. Evaporation yielded 31.3 g. of a yellow oil containing 2-bromo-4-trifluoromethylbenzylbromide formed in the above reaction. The compound was dissolved without further purification in 50 ml. of dry benzene. This solution was added in dropwise fashion to a sodium malonic ester solution prepared as follows: 7.7 g. of a 50 percent sodium hydride suspension in mineral oil was placed in a 500 ml. round bottom flask under a nitrogen atmosphere. The suspension was washed twice by decantation with 250 ml. portions of hexane. 100 ml. of DMF were then added and the solution cooled to 10° C. Next, 38.4 g. of diethylmalonate in 50 ml. of dried benzene were added with stirring. The resulting solution was stirred overnight at ambient temperature under a nitrogen atmosphere.

The reaction mixture formed by adding the benzyl bromide to the sodium malonic ester solution was stirred at room temperature for three days under a nitrogen atmosphere and was then poured over one liter of an ice-water mixture. The organic layer was separated and the aqueous layer extracted three times with ether. The ether extracts and organic layer were combined and the combined layers washed twice with water and once with saturated aqueous sodium chloride. The organic layer was dried and the solvents removed by evaporation in vacuo to yield 52.5 g. of a yellow oil containing diethyl 2-(2-bromo-4-trifluoromethylbenzyl) malonate formed in the above reaction plus some unreacted malonic ester starting material. Distillation of the residue through a Vigreaux column yielded a preliminary fraction boiling below 122° C. at 0.05 torr. containing chiefly unreacted malonic ester starting material, followed by several fractions boiling 122°–130° C. at 0.05 torr. weighing 24.6 g. and consisting of diethyl 2-(2-bromo-4-trifluoromethylbenzyl)malonate.

The diester thus prepared was saponified and decarboxylated according to the following procedure: 24.6 g. of diester were mixed with 92 ml. of anhydrous ethanol, 55 ml. of water and 37 ml. of 5 M aqueous sodium hydroxide. The solution was heated to reflux temperature overnight. The ethanol was removed by evaporation and the aqueous layer diluted with an additional 250 ml. of water. The aqueous layer was washed twice with ether and the ether extracts were discarded. The aqueous layer was then acidified with 12 N aqueous hydrochloric acid. 2-(2-bromo-4-trifluoromethylbenzyl) malonic acid formed in the above saponification was insoluble in the aqueous acidic layer and separated. The diacid was extracted into ether and the ether extract washed with water and with saturated aqueous sodium chloride. The ether extract was then dried and the ether evaporated therefrom to yield 23.4 g. of a yellow oil comprising 2-(2-bromo-4-trifluoromethylbenzyl)malonic acid. The diacid was decarboxylated by heating in an oil bath to about 180° C. for about 1.5 hours. The decarboxylation mixture containing β-(2-bromo-4-trifluoromethylphenyl) propionic acid was cooled and the acid dissolved in ether. The ether solution was dried. Evaporation of the ether yielded 16.9 g. of a yellow solid which yielded 8.1 g. of crystalline material from hexane. β-(2-Bromo-4-trifluoromethylphenyl) propionic acid thus purified melted at 80°–82° C.; $pK_a$ = 7.11.

Analysis Calc.: C, 49.43; H, 2.71; Br, 26.90; Found: C, 40.63; H, 2.66; Br, 27.14.

Following the procedure of *J. Org. Chem.*, 40, 2398 (1975), 7.4 g. of β-(2-bromo-4-trifluoromethylphenyl) propionic acid were dissolved in a mixture of 310 ml. of anhydrous THF and 62 ml. of hexane. The reaction mixture was cooled to −78° C. 32 ml. of 1.6 M n-butyl lithium in hexane were added thereto in dropwise fashion with stirring at such a rate that the pot temperature did not exceed −70° C. After the addition had been completed, the reaction mixture was poured over 200 ml. of 2 N aqueous hydrochloric acid. The organic layer was separated. The aqueous layer was washed with ether and the ether wash combined with the previous organic layer. The combined layer and extract were washed twice with 10 percent aqueous sodium carbonate, once with water and once with saturated aqueous sodium chloride, and were then dried. Evaporation of the solvent yielded a yellow oil containing a white solid which was separated by filtration. The filtrate was concentrated by evaporation in vacuo to yield 2.3 g. of a yellow oil comprising 6-trifluoromethyl-1-indanone formed in the above reaction. The compound showed strong carbonyl absorption at 1720 cm$^{-1}$ in the infrared. The oil was purified by distillation through a Vigreaux column to yield 1.7 g. of compound boiling in the range 76°–78° C. at 0.2 torr.

One gram of 6-trifluoromethyl-1-indanone was converted to the corresponding oxime by reaction with 1.92 g. of hydroxylamine hydrochloride in 4 ml. of pyridine and 20 ml. of anhydrous ethanol. The mixture was refluxed for 24 hours and then poured into cold water. The oxime precipitated and was separated by filtration. The filter cake was washed with hot water. 1.02 g. of a white powdery solid melting at 128°–32° C. comprising 6-trifluoromethyl-1-indanone oxime were obtained. The compound melted at 132°–7° C. after recrystallization from an ethyl acetate-cyclohexane solvent mixture.

A solution was prepared from 830 mg. of 6-trifluoromethyl-1-indanone oxime and 3 ml. of pyridine. 1 ml. of acetic anhydride was added and the reaction mixture stirred overnight at ambient temperature. The reaction mixture was then poured into 100 ml. of water from which an oil separated which oil later solidified. The solid was filtered and dried to yield 940 mg. of 6-trifluoromethyl-1-indanone oxime acetate. Recrystallization from cyclohexane yielded 770 mg. of the compound melting at 89°–93° C. after recrystallization from cyclohexane.

A solution of 770 mg. of the above oxime acetate was prepared in 5 ml. of THF. The solution was cooled in an ice bath to which was added, in dropwise fashion, 12 ml. of a 1 M diborane solution in THF. The reaction mixture was stirred at room temperature overnight after which time the solvent was removed by evaporation. 20 ml. of water were added to decompose any remaining borohydride. The reaction mixture was extracted twice with ether. The ether extracts were combined and the combined extracts washed twice with 50 ml. portions of 2 N aqueous hydrochloric acid. The acidic extracts were combined and made basic with 5 N aqueous sodium hydroxide. The alkaline layer was in turn extracted twice with ether. The ether extracts were combined and the combined extracts washed once with water, once with saturated aqueous sodium chloride and were then dried. Evaporation of the ether yielded 293 mg. of a yellow oil comprising 6-trifluoromethyl-1-aminoindane formed in the above reduction.

The hydrochloride salt of 6-trifluoromethyl-1-aminoindane was prepared by dissolving the amine base in ether and saturating the ethereal solution with gaseous HCl. The hydrochloride salt precipitated and was separated by filtration. 300 mg. of a colorless solid were obtained melting with partial decomposition at about 250° C. and showing a single spot on TLC were obtained. 6-Trifluoromethyl-1-aminoindane hydrochloride thus prepared melted above 260° C. after recrystallization from a methanol-ethyl acetate solvent mixture; $pK_a$ = 8.52.

Analysis Calc.: C, 50.76; H, 4.26; N, 5.92; Found: C, 50.60; H, 4.23; N, 6.10.

EXAMPLE 2

Preparation of 4-Trifluoromethyl-1-aminoindane

Following the procedure of Example 1, 3-nitro-2-methylbenzoic acid was fluorinated with SF$_4$ and HF to yield 2-nitro-6-trifluoromethyltoluene 16.9 g. of product were obtained from 18.1 g. of acid; boiling point = 35°–38° C. at 0.04 torr.

Analysis Calc.: C, 46.84; H, 2.95; N, 6.83; F, 27.78; Found: C, 46.58; H, 2.84; N, 7.01; F, 27.79.

187 g. of 2-nitro-6-trifluoromethyltoluene were reduced with hydrogen over a palladium-on-carbon catalyst to yield 153.9 g. of a red oil comprising 3-trifluoromethyl-2-methylaniline.

17.5 g. of the aniline were diazotized with nitrous acid and HBF$_4$ following *J.A.C.S.*, 58, 2308, (1936) to yield 16.7 g. of 2-methyl-3-trifluoromethylphenyldiazonium fluoborate. 16.7 g. of the fluoborate salt were heated in the presence of cupric bromide in DMSO to yield 10.4 g. of a colorless oil boiling at 72°-3° C. at 20.0 torr. consisting of 2-bromo-6-trifluoromethyltoluene.

Analysis Calc.: C, 40.20; H, 2.53; Br, 33.43; F, 23.84; Found: C, 40.24; H, 2.48; Br, 33.70; F, 23.79.

The methyl group of 2-bromo-6-trifluoromethyltoluene was brominated by reacting 47.8 g. of the toluene with 39.2 g. of N-bromosuccinimide under ultraviolet radiation. 77.5 g. of an orange oil comprising 2-bromo-6-trifluoromethylbenzyl bromide was obtained.

77.5 g. of the benzyl bromide were reacted with 76.9 g. of diethylmalonate sodium salt to yield diethyl 2-(2-bromo-6-trifluoromethylbenzyl) malonate. The diester boiled in the range 124°-137° C. at 0.35 torr; yield = 86.6 g.

Analysis Calc.: C, 45.36; H, 4.06; Found: C, 45.64; H, 4.20.

The diester was saponified and the resulting diacid decarboxylated to yield β-(2-bromo-6-trifluoromethylphenyl) propionic acid melting at 122°-126° C. 50.2 g. of acid were obtained from 86.1 g. of malonic ester. $pK_a$ = 7.01.

Analysis Calc.: C, 40.43; H, 2.71; Br, 26.90; F, 19.19; Found: C, 40.61; H, 2.47; Br, 26.91; F, 19.35.

Fourteen and nine-tenths grams of β-(2-bromo-6-trifluoromethylphenyl) propionic acid were cyclized with n-butyl lithium to yield 4-trifluoromethyl-1-indanone melting at about 32°-36° C.; yield = 6.2 g.; distilled at 67°-72° C. at 0.1 torr. 3 g. of the indanone were reductively aminated with ammonium acetate and sodium cyanoborohydride following the procedure of *J.A.C.S.*, 93, 287–97 (1971). According to this procedure, 3 g. of 4-trifluoromethyl-1-indanone, 691 mg. of sodium cyanoborohydride, 11.6 g. of ammonium acetate and 45 ml. of methanol were mixed in the presence of a 3A molecular sieve (to absorb water). The reaction mixture was stirred at room temperature for about 3 days. It was then cooled in an ice-water bath and acidified with 12 N aqueous hydrochloric acid. Methanol was removed by evaporation and an additional 100 ml. of water were added. The reaction mixture was filtered and the acidic filtrate extracted with ether. The ether extract was discarded and the acidic aqueous solution cooled and then made basic with 5N aqueous sodium hydroxide. The alkaline layer was extracted three times with ether, and the ether extracts combined. The combined extracts were washed with saturated aqueous sodium chloride and then dried. Evaporation of the ether yielded 2 g. of an oil comprising 4-trifluoromethyl-1-aminoindane. The hydrochloride salt was made by the process of Example 1. Crystalline 4-trifluoromethyl-1-aminoindane hydrochloride thus prepared melted at 207°-211° C. with decomposition after recrystallization from an ethyl acetate-methanol solvent mixture; $pK_a$ = 8.58.

Analysis Calc.: C, 50.54; H, 4.67; N, 5.89; F, 23.98; Found: C, 50.65; N, 4.64; N, 5.84; F, 23.89.

EXAMPLE 3

Preparation of 7-trifluoromethyl-1-aminoindane

Following the procedure of Example 1, 2-nitro-3-methylbenzoic acid is fluorinated with $SF_4$ and HF to yield 2-nitro-3-trifluoromethyltoluene. Reduction of the nitro group yielded 6-trifluoromethyl-2-methylaniline which is diazotized to form 2-methyl-6-trifluoromethylphenyldiazonium fluoborate. Decomposition of the fluoborate salt in the presence of cupric bromide yields 2-bromo-3-trifluoromethyltoluene. Bromination of the side chain with N-bromosuccinimide in the presence of ultraviolet light yields 2-bromo-3-trifluoromethylbenzyl bromide. Reaction of the benzyl bromide with diethyl malonate sodium salt yields diethyl 2-(2-bromo-3-trifluoromethylbenzyl) malonate. This diester is saponified and decarboxylated to yield β-(2-bromo-3-trifluoromethylphenyl) propionic acid. Cyclization of the propionic acid yields 7-trifluoromethyl-1-indanone which is reductively aminated to yield 7-trifluoromethyl-1-aminoindane, purified as the hydrochloride salt.

EXAMPLE 4

Preparation of 5-trifluoromethyl-1-aminoindane

Following the procedure of Example 1, 3-methyl-4-nitrobenzoic acid is fluorinated with $SF_4$ and HF to yield 2-nitro-5-trifluoromethyltoluene. Reduction of the nitro group yields 2-methyl-4-trifluoromethylaniline which, upon diazotization in the presence of $HBF_4$ and sodium nitrite, gives 2-methyl-4-trifluoromethylphenyldiazonium fluoborate. Reaction of the diazonium salt with cupric bromide yields 2-bromo-5-trifluoromethyltoluene. Bromination of the side chain with N-bromosuccinimide in the presence of ultraviolet light yields 2-bromo-5-trifluoromethylbenzyl bromide. Reaction of the benzyl bromide with sodium diethyl malonate gives diethyl 2-(2-bromo-5-trifluoromethylbenzyl) malonate which upon saponification and decarboxylation yields β-(2-bromo-5-trifluoromethylbenzyl) propionic acid. Cyclization of the propionic acid yields 5-trifluoromethyl-1-indanone which compound is reductively amminated to yield 5-trifluoromethyl-1-aminoindane, purified as the hydrochloride salt.

EXAMPLE 5

Preparation of Salts

Acid addition salts of the 1-aminoindanes of this invention are prepared by various procedures. In the above examples, in which the hydrochloride salt was prepared, an ether solution of the 1-aminoindane was prepared and gaseous HCl passed into this solution. The hydrochloride salt, being insoluble in the ethereal solvent, precipitated and was isolated by filtration. Other solid acids which are soluble in ether can be utilized in the above procedure by adding an equimolar amount of the acid, such as maleic or succinic acid to the ethereal solution of the base. An alternative procedure is to employ, for example, an alcoholic solution of the 1-aminoindane and add the acid thereto in the form of an alcoholic solution. For example, the hydrochloride salt can be prepared by dissolving the 1-aminoindane in ethanol and adding equimolar quantity of a suitable acid to the solution. Ordinarily, with an ethanolic solvent, the acid addition salt is soluble and is isolated by evaporating the solvent. This last procedure is particularly useful for preparing the sulfates, phosphates, and the like salts which are ordinarily soluble in water and aqueous ethanol.

The compounds of this invention, either in the form of the free base, or as a pharmaceutically-acceptable acid addition salt thereof, are enzyme inhibitors. In particular, as previously stated, they are inhibitors of norephineprine N-methyl transferase [PNMT or phenethanolamine N-methyl transferase - - see Axelrod, *J. Bio. Chem.*, 237, 1657 (1962)]. Compounds which inhibit the conversion of norephineprine to ephineprine are capable of lowering a high ephineprine-norephineprine ratio in mammals, a physiological condition frequently associated with essential hypertension. The compounds of this invention are thus capable of ameliorating the ephineprine-norephineprine imbalance in essential hypertension, an important aspect of the treatment of this disease state. The effectiveness of the compounds as N-methyl transferase inhibitors has been measured in vitro employing NMT from rabbit adrenals. By using a series of decreasing concentration of the inhibiting amine, usually starting with $1 \times 10^{-4}M$ continuing with $3 \times 10^{-5}M$, $1 \times 10^{-5}M$, etc., it was possible to determine a concentration at which the 50 percent inhibition of NMT was achieved. The negative reciprocal logarhithm ($pI_{50}$) of this number was also calculated as a useful index. Table 1, which follows, summarizes the information thus obtained; i.e., the determination of enzyme inhibition activity for the compounds of this invention. In the table, column 1 gives the name of the compound and column 2, the $pI_{50}$.

TABLE 1

| Name | $pI_{50}$ |
|---|---|
| 4-trifluoromethyl-1-aminoindane hydrochloride | 6.63 |
| 6-trifluoromethyl-1-aminoindane hydrochloride | 4.19 |

The compounds of this invention are used as NMT inhibitors preferably in the form of a pharmaceutically-acceptable acid addition salt. These salts can be mixed with one or more standard pharmaceutical excipients and loaded into empty telescoping gelatin capsules or compressed into tablets for oral administration. Aqueous solutions of these salts can be employed for parenteral administration, with an isotonic solution being particularly adapted for IV use.

I claim:
1. A compound of the formula

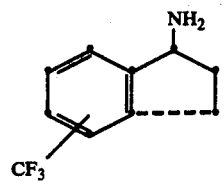

and pharmaceutically-acceptable acid addition salts thereof.

2. A compound according to claim 1, said compound being 4-trifluoromethyl-1-aminoindane.

3. The hydrochloride salt of the amine base of claim 2.

4. A compound according to claim 1, said compound being 6-trifluoromethyl-1-aminoindane.

5. The hydrochloride salt of the compound of claim 4.

* * * * *